(12) United States Patent
Cheng et al.

(10) Patent No.: US 11,892,435 B2
(45) Date of Patent: Feb. 6, 2024

(54) NMR METHODS FOR MEASURING PH IN ORAL CARE, HOME CARE AND PERSONAL CARE PRODUCTS

(71) Applicant: Colgate-Palmolive Company, New York, NY (US)

(72) Inventors: Chi-Yuan Cheng, Hillsborough, NJ (US); Zhigang Hao, Bridgewater, NJ (US); Long Pan, Somerset, NJ (US); Zolijargal Balsandorj, Piscataway, NJ (US)

(73) Assignee: Colgate-Palmolive Company, New York, NY (US)

( * ) Notice: Subject to any disclaimer, the term of this patent is extended or adjusted under 35 U.S.C. 154(b) by 875 days.

(21) Appl. No.: 16/703,985

(22) Filed: Dec. 5, 2019

(65) Prior Publication Data

US 2020/0182841 A1     Jun. 11, 2020

Related U.S. Application Data

(60) Provisional application No. 62/778,165, filed on Dec. 11, 2018.

(51) Int. Cl.
   *G01N 33/15*     (2006.01)
   *G01N 24/08*     (2006.01)
   (Continued)

(52) U.S. Cl.
   CPC ........... *G01N 31/221* (2013.01); *G01N 24/08* (2013.01); *G01R 33/465* (2013.01)

(58) Field of Classification Search
   CPC ...... G01N 33/15; G01N 24/08; G01N 31/221; G01R 33/465
   (Continued)

(56) References Cited

U.S. PATENT DOCUMENTS 5,639,906 A * 6/1997 London ................. C07C 217/86
                                                                  562/452
6,596,258 B1   7/2003 Ballesteros Garcia et al.
(Continued)

OTHER PUBLICATIONS

Fujii, H. et al, Bulletin of the Chemical Society of Japan 1979, 52, 2051-2055.*
(Continued)

*Primary Examiner* — Arlen Soderquist (57) ABSTRACT

Methods for measuring pH of gel, paste, colloid, and aqueous solutions, such as a consumer product, a food product, a pet food product, a beverage product, a pharmaceutical product, and/or a medical product, are provided. The method may include preparing a calibration curve of a chemical species including or having an acid dissociation constant. Preparing the calibration curve may include plotting a chemical shift of the chemical species relative to pH. The method may also include determining a chemical shift of a gel, paste, and colloid, aqueous solutions, such as a consumer product, a food product, a pet food product, a beverage product, a pharmaceutical product, and/or a medical product, including the chemical species. The method may further include determining the pH of the gel, paste, colloid, and aqueous solutions, such as a consumer product, a food product, a pet food product, a beverage product, a pharmaceutical product, and/or a medical product, with the chemical shift of the product and the calibration curve.

14 Claims, 3 Drawing Sheets

(51) Int. Cl.
  *G01N 31/22*  (2006.01)
  *G01R 33/465* (2006.01)
(58) Field of Classification Search
  USPC .................................................. 436/163, 173
  See application file for complete search history.

(56) References Cited

U.S. PATENT DOCUMENTS

| | | | |
|---|---|---|---|
| 10,295,487 B2 | 5/2019 | Huang et al. | |
| 2016/0109390 A1* | 4/2016 | Chi ..................... | G01R 33/4804 324/309 |
| 2016/0252532 A1 | 9/2016 | Schilling et al. | |

OTHER PUBLICATIONS

Barton, J. K. et al, Proceedings of the National Academy of Sciences of the United States of America 1980, 77, 2470-2473.*
Smith, R. E. et al, Helvetica Chimica Acta 1980, 63, 2302-2311.*
Jayasundar, R. et al, NMR in Biomedicine 1992, 5, 360-363.*
Rolin, D. et al, Australian Journal of Plant Physiology 2000, 27, 61-69.*
Vistad, O. B. et al, Chemistry of Materials 2003, 15, 1650-1654.*
Szakacs, Z. et al, Analytica Chimica Acta 2004, 522, 247-258.*
Tynkkynen, T. et al, Analytica Chimica Acta 2009, 648, 105-112.*
Holzgrabe, U., Progress in Nuclear Magnetic Resonance Spectroscopy 2010, 57, 229-240.*
Halliday, N. A. et al, Journal of Physical Chemistry B 2010, 114, 13745-13751.*
Orgovan, G, et al, Journal of Pharmaceutical and Biomedical Analysis 2011, 54, 958-964.*
Kraszni, M. et al, Analytical and Bioanalytical Chemistry 2013, 405, 5807-5816.*
Scholz, D. J. et al, Magnetic Resonance in Medicine 2015, 73, 2274-2282.*
Wallerstein, J. et al, Journal of the American Chemical Society 2015, 137, 3093-3101.*
Jensen, P. R. et al, Chemical Communications 2016, 52, 2288-2291.*
Duwel, S. et al, Nature Communications 2017, 8, paper 15126, 9 pages.*
Siriphanich, H. et al, Journal of the American Society for Horticultural Science 1986, 111, 73-77.*
Robitaille, P.- M. L. et al, Journal of Magnetic Resonance 1991, 92, 73-84.*
Chacko, V. P. et al, American Journal of Physiology 1993, 264, C755-C760.*
Ackerman, J. J. H. et al, Magnetic Resonance in Medicine 1996, 36, 674-683.*
Gallagher, F. A. et al, NMR in Biomedicine 2011, 24, 1006-1015.*
Njus, D. et al, Biochemistry 1978, 17, 4337-4343. (Year: 1978).*
Burt, C. T. et al, Cryobiology 1996, 33, 62-69. (Year: 1996).*
Burke, P. A., Proceedings International Symposium on Controlled Release of Bioactive Materials 1996, 23, 133-134. (Year: 1996).*
Gerardin, C. et al, Chemistry of Materials 1999, 11, 1285-1292. (Year: 1999).*
Taulelle, F. et al, Colloids and Surfaces A: Physicochemical and Engineering Aspects 1999, 158, 299-311. (Year: 1999).*
Jarlbring, M. et al, Langmuir 2006, 22, 4787-4792. (Year: 2006).*
Wong-Moon, K. C. et al, Molecular Pharmaceutics 2008, 5, 654-664 with 4 pages of supporting information. (Year: 2008).*
Deng, D. et al, Spectroscopy Letters 2009, 42, 334-340. (Year: 2009).*
Gerken, J. B., Journal of Fluorine Chemistry 2011, 132, 68-70. (Year: 2011).*
Zaid, A. N., Asian Journal of Pharmaceutics 2011, 5, 125-128. (Year: 2011).*
Marzorati, M. et al, Analytical Chemistry 2013, 85, 3822-3827 with 12 pages of supporting information. (Year: 2013).*
Surface, J. A. et al, Environmental Science & Technology 2015, 49, 1631-1638. (Year: 2015).*
Tawakoli, P. N. ewt al, Swiss Dental Journal 2015, 125, 1210-1219. (Year: 2015).*
Wallace, M. et al, Soft Matter 2015, 11, 7739-7747 with 24 pages of supplementary material. (Year: 2015).*
Korenchan, D. E. et al, Chemical Communications 2016, 52, 3030-3033 with 12 pages of supplementary material. (Year: 2016).*
Warnida, H. et al, Jurnal Sains Farmasi & Klinis 2016, 3, 42-49. (Year: 2016).*
Wallace, M. et al, Soft Matter 2017, 13, 1716-1727 with 41 pages of supplementary material. (Year: 2017).*
"Consumer and Business Products" undated, 7 pages, downloaded from https://www.encyclopedia.com/finance/finance-and-accounting-magazines/consumer-and-business-products.*
"Consumer Products" undated, 13 pages, downloaded from https://www.wallstreetoasis.com/resources/skills/economics/consumer-products.*
Seo, Y. et al, Journal of Biochemistry 1983, 94, 729-734. (Year: 1983).*
Yoza, N. et al, Fresenius' Journal of Analytical Chemistry 1994, 348, 633-638. (Year: 1994).*
Shanks, J. V., Current Issues in Molecular Biology 2001, 3, 15-26. (Year: 2001).*
Rusu-Balaita, L. et al, Polymer Bulletin 2003, 50, 91-98. (Year: 2003).*
Moret, S. et al, Dalton Transactions 2013, 42, 4353-4356. (Year: 2013).*
Stephane, P., MOJ Toxicology 2015, 1, paper 00003, 11 pages. (Year: 2015).*
Bonjour, J. L. et al, Journal of CHemical Education 2015, 92, 529-533. (Year: 2015).*
Hyland, B. W. et al, Clinical Oral Investigations 2015, 19, 1395-1404. (Year: 2015).*
Babu, G. et al, International Journal of Pharmaceutical Sciences Review and Research 2016, 39, 134-137. (Year: 2016).*
"Cleaning Agent" Wikipedia undated, downloaded Jul. 17, 2023 from https://en.wikipedia.org/wiki/Cleaning_agent. (Year: 2023).*
"Personal Care Products" Wikipedia undated, downloaded Jul. 17, 2023 from https://en.wikipedia.org/wiki/Personal_care_products. (Year: 2023).*
Baryshnikova et al., "Internal pH indicators for biomolecular NMR", Journal of Biomolecular NMR, Kluwer Academic Publishers, 41(1):5-7 (2008).
International Search Report and the Written Opinion of the International Searching Authority issued in International Application PCT/US2019/064581 dated Mar. 19, 2020.
Mistry et al., "The relative hydrolytic reactivities of pyrophosphites and pyrophosphates", Organic & Biomolecular Chemistry, 11(34):5727-5733 (2013).
Popov et al., "Guidelines for NMR measurements for determination of high and low pKa values (IUPAC Technical Report)", International Union of Pure & Applied Chemistry, 78(3):663-675 (2006).
Wallace et al., "Titrations without the Additions: The Efficient Determination of p K a values using NMR Imaging Techniques", Analytical Chemistry,90(6):4160-4166 (2018).
Ferreira Do Amaral, et al., 2015, "Choice of toothpaste for the elderly: an in vitro study," Braz. Oral Res [online] 29(1):1-7.
Martin et al., 1982, "A 31P nuclear magnetic resonance study of intracellular pH of plant cells cultivated in liquid medium," Plant Physiology 70:1156-1161.
Price et al., 2000, "The pH of tooth whitening products," J. Can. Dental Assoc. 66:421-426.
Roberts et al., 1980, "Estimation of cytoplasmic and vaculolar pH in higher plant cells by 31P NMR," Nature 283:870-872.

* cited by examiner

NMR METHODS FOR MEASURING PH IN ORAL CARE, HOME CARE AND PERSONAL CARE PRODUCTS

CROSS-REFERENCE TO RELATED APPLICATIONS

This application claims priority to U.S. Provisional Patent Application No. 62/778,165, filed Dec. 11, 2018, which is incorporated herein by reference in its entirety.

BACKGROUND

The accurate pH value of compositions, including gel, paste, colloid, and aqueous solutions, such as a consumer product, a food product, a pet food product, a beverage product, a pharmaceutical product, and/or a medical product, is an integral factor related to the health of consumers. It is also a critical factor related to the stability and quality of one or more key ingredients in a consumer product, food product, pet food product, beverage product, pharmaceutical product, and/or a medical product. For example, in oral care products, the stability of toothpastes is often related or intimately tied to changes in the pH thereof. The current method of measuring the pH of toothpastes via a pH meter or electrode, however, is known to be inaccurate and unreliable due to many factors, such as the inhomogeneity and relative low water content of the toothpastes. Further, a pH electrode measures the pH by determining the total amount of hydrogen ions, which is difficult and inaccurate in neat or undiluted toothpastes, which contain less than or equal to about 80 weight % of water. Additionally, efforts to increase the water content by preparing a slurry, and subsequently measuring the pH of the slurry have also proven to be inaccurate, as the added water may alter or influence respective structures and dynamics of one or more chemical species in the toothpaste, which may alter the measured pH.

What is needed, then, are improved methods for measuring pH of different compositions, including but not limited to gel, paste, colloid, and aqueous solutions, such as consumer products, food products, pet food products, beverage products, pharmaceutical products, and/or medical products.

BRIEF SUMMARY

This summary is intended merely to introduce a simplified summary of some aspects of one or more implementations of the present disclosure. Further areas of applicability of the present disclosure will become apparent from the detailed description provided hereinafter. This summary is not an extensive overview, nor is it intended to identify key or critical elements of the present teachings, nor to delineate the scope of the disclosure. Rather, its purpose is merely to present one or more concepts in simplified form as a prelude to the detailed description below.

The foregoing and/or other aspects and utilities embodied in the present disclosure may be achieved by providing a method for determining pH of a composition, including but not limited to a gel, a paste, a colloid, and/or an aqueous solution, such as a consumer product (eg. an oral care product), a food product, a pet food product, a beverage product, a pharmaceutical product, and/or a medical product. The method may include preparing a calibration curve of a chemical species including or having an acid dissociation constant. Preparing the calibration curve may include plotting a chemical shift of the chemical species relative to pH. The method may also include determining a chemical shift of a composition, including but not limited to a gel, a paste, a colloid, and/or an aqueous solution including the chemical species. The method may further include determining the pH of the composition, including but not limited to a gel, a paste, a colloid, and/or an aqueous solution, with the chemical shift of composition and the calibration curve.

In at least one implementation, the chemical species may include a carbonyl group, optionally, a carboxyl group. In another implementation, the chemical species may include a bicarbonate ion or a carbonate ion. In at least one implementation, the chemical shift of the composition, including but not limited to a gel, a paste, a colloid, and/or an aqueous solution, may be determined via carbon-13 nuclear magnetic resonance spectroscopy ($^{13}C$ NMR).

In at least one implementation, the chemical species comprises a phosphate group. In at least one implementation, the chemical species may include one or more of tetrasodium pyrophosphate, tetrapotassium pyrophosphate, phosphoric acid, sodium monofluorophosphate, dicalcium phosphate dehydrate, sodium triphosphate, sodium hexametaphosphate, or combinations thereof. In at least one implementation, the chemical species may include phosphoric acid. In at least one implementation, the chemical shift of the composition is determined via phosphorus-31 nuclear magnetic resonance spectroscopy ($^{31}P$ NMR).

In at least one implementation, the composition, including but not limited to a gel, a paste, a colloid, and/or an aqueous solution, may include water in an amount less than 80 weight %, optionally, less than 70 weight %, less than 60 weight %, or less than 50 weight %, based on a total weight of the product.

In at least one implementation, the composition, including but not limited to a gel, a paste, a colloid, and/or an aqueous solution, may be a consumer product, a food product, a pet food product, a beverage product, a pharmaceutical product, and/or a medical product. The consumer product may include, for example, an oral care product, a home care product, and/or a personal care product. In at least one implementation, the oral care product may be toothpaste.

In at least one implementation, the chemical shift of the composition, including but not limited to a gel, a paste, a colloid, and/or an aqueous solution, may be determined without diluting the composition.

In at least one implementation, the chemical shift of the composition, including but not limited to a gel, a paste, a colloid, and/or an aqueous solution, may be determined without pre-processing the composition.

In at least one implementation, determining the chemical shift of the composition, including but not limited to a gel, a paste, a colloid, and/or an aqueous solution, including the chemical species may include preparing a slurry of the composition.

In at least one implementation, preparing the calibration curve of the chemical species may include preparing a plurality of solutions including the chemical species, wherein each of the plurality of solutions has or includes a different pH. Preparing the calibration curve of the chemical species may also include determining a chemical shift of each of the plurality of solutions having the different pH.

In at least one implementation, preparing the calibration curve of the chemical species may further include preparing a plot of the chemical shift of each of the plurality of solutions with respect to the pH of each of the plurality of solutions, and fitting a curve to the plot to prepare the calibration curve.

Further areas of applicability of the present disclosure will become apparent from the detailed description provided hereinafter. It should be understood that the detailed description and specific examples, while indicating some typical aspects of the disclosure, are intended for purposes of illustration only and are not intended to limit the scope of the disclosure.

BRIEF DESCRIPTION OF THE DRAWINGS

The present disclosure is best understood from the following detailed description when read with the accompanying Figures. It is emphasized that, in accordance with the standard practice in the industry, various features are not drawn to scale. In fact, the dimensions of the various features may be arbitrarily increased or reduced for clarity of discussion.

DETAILED DESCRIPTION

The following description of various typical aspect(s) is merely exemplary in nature and is in no way intended to limit the disclosure, its application, or uses.

As used throughout this disclosure, ranges are used as shorthand for describing each and every value that is within the range. It should be appreciated and understood that the description in a range format is merely for convenience and brevity, and should not be construed as an inflexible limitation on the scope of any embodiments or implementations disclosed herein. Accordingly, the disclosed range should be construed to have specifically disclosed all the possible subranges as well as individual numerical values within that range. As such, any value within the range may be selected as the terminus of the range. For example, description of a range such as from 1 to 5 should be considered to have specifically disclosed subranges such as from 1.5 to 3, from 1 to 4.5, from 2 to 5, from 3.1 to 5, etc., as well as individual numbers within that range, for example, 1, 2, 3, 3.2, 4, 5, etc. This applies regardless of the breadth of the range.

Unless otherwise specified, all percentages and amounts expressed herein and elsewhere in the specification should be understood to refer to percentages by weight. The amounts given are based on the active weight of the material.

Additionally, all numerical values are "about" or "approximately" the indicated value, and take into account experimental error and variations that would be expected by a person having ordinary skill in the art. It should be appreciated that all numerical values and ranges disclosed herein are approximate values and ranges, whether "about" is used in conjunction therewith. It should also be appreciated that the term "about," as used herein, in conjunction with a numeral refers to a value that may be ±0.01% (inclusive), ±0.1% (inclusive), ±0.5% (inclusive), ±1% (inclusive) of that numeral, ±2% (inclusive) of that numeral, ±3% (inclusive) of that numeral, ±5% (inclusive) of that numeral, ±10% (inclusive) of that numeral, or ±15% (inclusive) of that numeral. It should further be appreciated that when a numerical range is disclosed herein, any numerical value falling within the range is also specifically disclosed.

As used herein, "free" or "substantially free" of a material may refer to a composition, component, or phase where the material is present in an amount of less than 10.0 weight %, less than 5.0 weight %, less than 3.0 weight %, less than 1.0 weight %, less than 0.1 weight %, less than 0.05 weight %, less than 0.01 weight %, less than 0.005 weight %, or less than 0.0001 weight % based on a total weight of the composition, component, or phase.

All references cited herein are hereby incorporated by reference in their entireties. In the event of a conflict in a definition in the present disclosure and that of a cited reference, the present disclosure controls.

The present inventors have surprisingly and unexpectedly discovered that measuring the pH of composition, including but not limited to a gel, a paste, a colloid, and/or an aqueous solution, such as a consumer product, food product, beverage product, pharmaceutical product, and/or a medical product, via nuclear magnetic resonance (NMR) methods disclosed herein is relatively more precise, accurate, and/or reliable than measuring the pH of the composition via a conventional pH meter based on a pH electrode. Specifically, the standard deviation of the pH measured via the NMR method is unexpectedly, significantly, and surprisingly lower than the standard deviation of the pH measured via the conventional pH meter method. It was further surprisingly and unexpectedly discovered that the method of measuring the pH of the composition via the NMR spectrometer could be used to measure the pH of compositions including phosphoric acid, sodium bicarbonate, sodium lactate, lactic acid, and/or chemical species or molecular entities that produce orthophosphate ($PO_4$) as a byproduct, such as sodium monofluorophosphate (MFP), dicalcium phosphate dehydrate (Dical), tetrapotassium pyrophosphate (TKPP), sodium triphosphate (STPP), and tetrasodium pyrophosphate (TSPP).

The present disclosure may provide methods for determining a pH of a composition, including but not limited to a gel, a paste, a colloid, and/or an aqueous solution, for example a consumer product, food product, beverage product, pharmaceutical product, and/or a medical product. The method for determining the pH of the composition may include preparing a calibration curve of one or more chemical species or molecular entities having an acid dissociation constant ($pK_a$), determining a chemical shift of the product including the chemical species or molecular entity, and determining the pH of the product with the chemical shift of the product and the calibration curve. As further described herein, the calibration curve of the chemical species or molecular entity may be a plot of a chemical shift of the chemical species or molecular entity relative to pH.

The compositions may be or include, but are not limited to, any solution with water as a solvent. The aqueous solution may include water in an amount of less than or equal to about 80 weight %, based on a total weight of the solution. For example, the aqueous solution may include water in an amount of less than or equal to 80 weight %, less than or equal to 75 weight %, less than or equal to 70 weight %, less than or equal to 65 weight %, less than or equal to 60 weight %, less than or equal to 55 weight %, less than or equal to 50 weight %, less than or equal to 45 weight %, less than or equal to 40 weight %, less than or equal to 35 weight %, less than or equal to 30 weight %, less than or equal to 25 weight %, or less, based on a total weight of the composition or the product. It should be appreciated that measuring the pH of the composition, including but not limited to a gel, a paste, a colloid, and an aqueous solution, consumer product, substance, component, or material via a conventional pH meter is inaccurate, exhibits relatively large variations or variability, and/or lacks precision when the water content is less than or equal to about 80 weight %. The composition measured may be natural or manmade.

The composition, including but not limited to a gel, a paste, a colloid, and/or an aqueous solution, may be or include a consumer product, a food product, a pet food product, a beverage product, a pharmaceutical product, and/or a medical product. The consumer products may be or include, but are not limited to, home care products (e.g., cleansers, dish soaps, detergents, etc.), personal care products (e.g., deodorants, gels, hair care products, lotions, etc.), oral care products, or the like, or any combination thereof. In an exemplary implementation, the consumer products include an oral care product. The oral care product or the oral care composition thereof may form at least a portion of or be used in one or more oral care products. Illustrative oral care products may be or include, but are not limited to, a toothpaste (dentifrice), a prophylactic paste, a tooth powder, a tooth polish, a tooth gel (e.g., a whitening gel), a chewing gum, a lozenge, a mouthwash, a whitening strip, a paint-on gel, varnish, veneer, syringe or dental tray including a gel or paste, a gel or paste coated on an application support, such as dental floss or a toothbrush (e.g., a manual, electric, sound, a combination thereof or ultrasound toothbrush), or the like. In a preferred implementation, the oral care composition may be or may form at least a portion of a mouthwash.

The composition, including but not limited to a gel, a paste, a colloid, and/or an aqueous solution, may include one or more chemical species, molecular species or entities, or the like, or combination thereof that has or includes an acid dissociation constant. As used herein, the term or expression "molecular entity" may refer to any constitutionally or isotopically distinct atom, molecule, ion, ion pair, radical, radical ion, complex, conformer, or the like, identifiable as a separately distinguishable entity. As used herein, the term or expression "chemical species" may refer to any atom, molecule, molecular fragment, ion, or the like, that may be subjected to a chemical process or a measurement. For example, a chemical species may be an ensemble of chemically identical molecular entities that can explore the same set of molecular energy levels on the time scale of the experiment.

The one or more chemical species or molecular entity may each include one or more functional groups, such as a protonated functional group. Illustrative functional groups may be or include, but are not limited to, a carboxyl group, a phosphate group, a carbonyl group, a hydroxyl group, an amine group, an ether group, a thiol group, an alkane group, an alkene group, a sulfoxide group, an alkyne group, a nitrile groups, a ketone group, an aldehyde group, an alcohol group, a sulfonic group, or the like, or combinations thereof. In at least one implementation, the chemical species or molecular entity includes a carbonyl group, a carboxyl group, or combinations thereof. In another implementation, the chemical species or molecular entity includes a phosphate group. Illustrative chemical species or molecular entities may be or include, but are not limited to, bicarbonate, carbonate, tetrasodium pyrophosphate (TSPP), tetrapotassium pyrophosphate (TKPP), sodium triphosphate (STPP), sodium hexametaphosphate (SHMP), phosphoric acid, sodium monofluorophosphate (MFP), dicalcium phosphate dehydrate (Dical), or the like, or combinations thereof. In a preferred implementation, the chemical species or molecular entity includes one or more of bicarbonate, carbonate, phosphoric acid, or combinations thereof.

Calibration Curve

As discussed above, the method may include preparing a calibration curve of one or more chemical species or molecular entities having an acid dissociation constant. Preparing the calibration curve may include preparing a plurality of standard or known solutions or samples including any one or more of the chemical species or molecular entities, where each of the plurality of solutions or samples has a different pH. The pH of each of the plurality of solutions or samples may be acidic, neutral, or basic. For example, the pH of each of the plurality of solutions or samples may be from about 1, about 2, about 3, about 4, about 5, about 6, or about 7 to about 8, about 9, about 10, about 11, about 12, about 13, or about 14. It should be appreciated that the pH of each of the plurality of solutions or samples may be adjusted to any desired pH by combining one or more bases, one or more acids, or a combination of one or more bases and one or more acids therewith.

Preparing the calibration curve may also include determining or measuring a chemical shift of each of the plurality of solutions at each of the respective pH. The chemical shift of each of the plurality of solutions may be determined or measured by nuclear magnetic resonance (NMR) spectroscopy. It should be appreciated that the type of NMR spectroscopy utilized for measuring the chemical shift may be at least partially determined by the chemical species or the molecular entity being monitored or included in the composition. For example, samples and/or solutions including bicarbonate or carbonate as the chemical species or molecular entity may utilize carbon-13 NMR spectroscopy. In another example, samples and/or solutions including a chemical species or molecular entity having a phosphate group may utilize phosphorus-31 NMR spectroscopy. While carbon-13 NMR spectroscopy and phosphorus-31 NMR spectroscopy are demonstrated, it should be appreciated that other types of NMR may be utilized, such as NMR that measures the chemical shift of any one or more of hydrogen nuclei, fluorine, boron, nitrogen, oxygen, tin, or the like, or any combination thereof, each of which have distinctive magnetic properties.

Preparing the calibration curve may also include preparing a plot of the chemical shift of each of the plurality of samples and/or solutions with respect to the pH of each of the plurality of samples and/or solutions. As discussed above, the chemical species or molecular entity may be or include carbonate or bicarbonate. Because bicarbonate ($HCO_3^-$) and carbonate ($CO_3^{2-}$) undergo a fast exchange in an NMR timescale, the observed C-13 NMR chemical shift of the carboxyl group ($\delta$) can be expressed as the weighted average of the C-13 chemical shift between $HCO_3^-$($\delta HCO_3$) and $CO_3^{2-}$($\delta CO_3^2$) according to equation (1):

$$\delta_C = xHCO_3^- \delta HCO_3^- + xCO_3^2 \delta CO_3^2 \quad (1)$$

where $xHCO_3^-$ and $xCO_3^2$ are the molar ratio of bicarbonate and carbonate in the sample, respectively. The pH of bicarbonate may be expressed in terms of the pKa of bicarbonate, as represented by Equation (2):

$$pH = pKa + \log\left[(\delta_C - \delta HCO_3^-)/(\delta CO_3^{2-} - \delta_C)\right] \quad (2).$$

Figure 1:
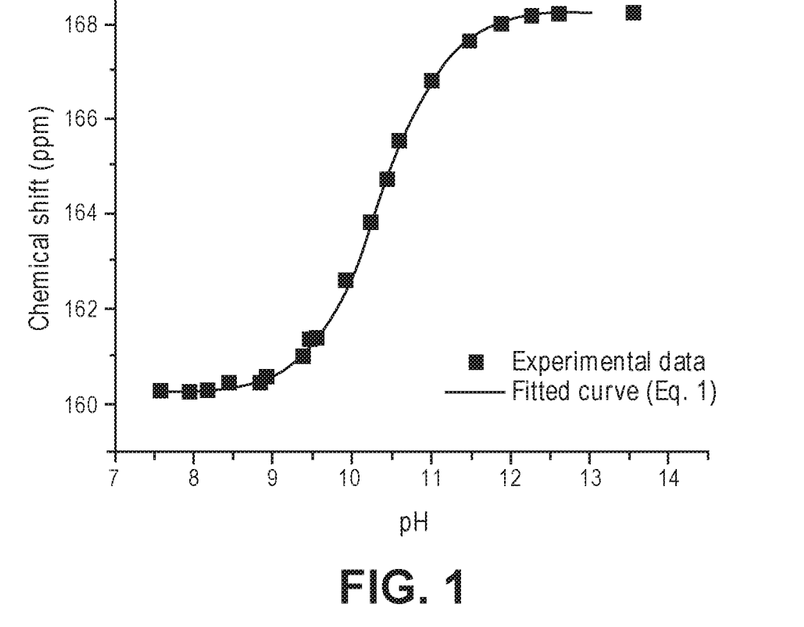
FIG. 1 illustrates a plot of the chemical shift of each of the plurality of solutions including bicarbonate and carbonate with respect to pH, according to one or more implementations disclosed.

FIG. 1 illustrates a plot of the chemical shift of each of the plurality of solutions including bicarbonate and carbonate with respect to pH.

As further discussed above, the chemical species or molecular entity may be or include a phosphate group, where the observed P-31 chemical shift can be expressed according to equation (3):

$$\delta_P = xH_2PO_4^- \delta H_2PO_4^- + xHPO_4^- \delta HPO_4^- \quad (3)$$

where $xH_2PO_4^-$ and $xHPO_4^-$ are the molar ratio of two monophosphate species in the sample. The pH of the phosphate group may be expressed in terms of the pKa of phosphate, as represented by Equation (4):

$$pH = pKa + \log[(\delta_P - \delta H_2PO_4^-)/(\delta HPO_4^{2-} - \delta_P)] \quad (4)$$

Figure 3:
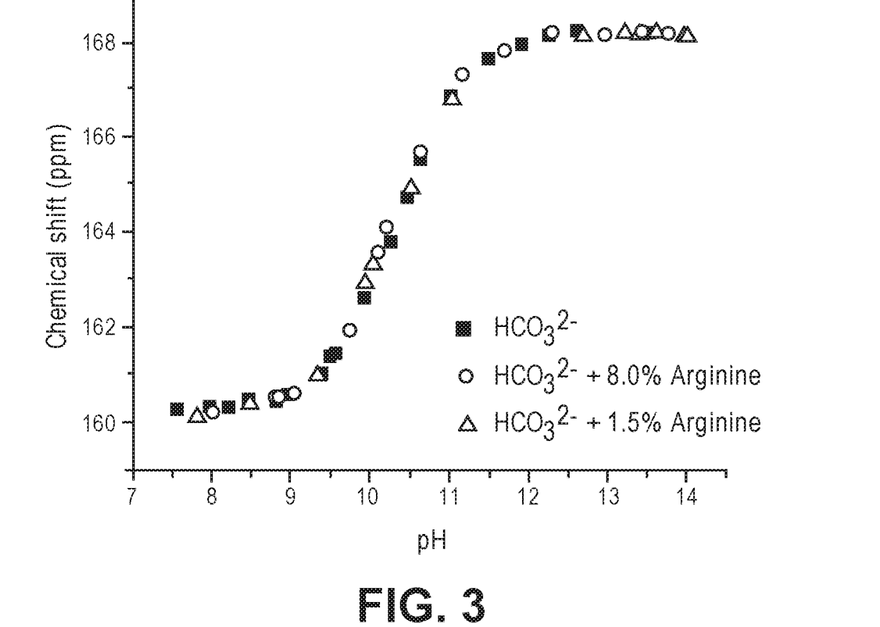
FIG. 3 illustrates a plot of the chemical shift of a plurality of solutions including bicarbonate, carbonate, and varying amounts of arginine with respect to pH, according to one or more implementations disclosed.

FIG. 3 illustrates a plot of the chemical shift of each of the plurality of solutions including a phosphate group with respect to pH.

In at least one implementation, the chemical species or molecular or molecular entity may be or include a carboxyl group, such as the carboxyl group of a lactic acid, where the observed C-13 chemical shift can be expressed according to equation (5):

$$pH = pKa + \log[(\delta_C - \delta CO_2H)/(\delta CO_2^- - \delta_C)] \quad (5)$$

Figure 2:
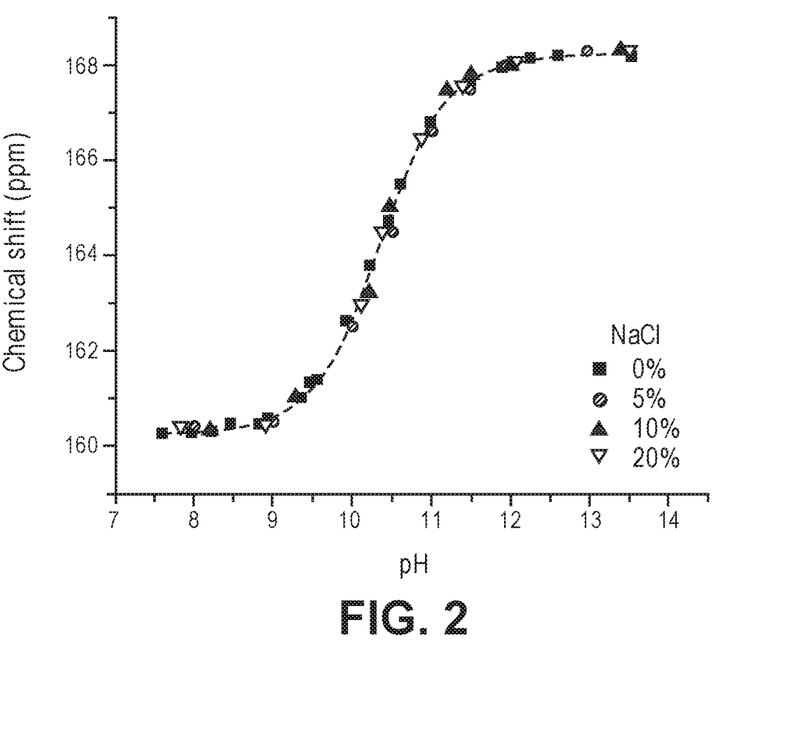
FIG. 2 illustrates a plot of the chemical shift of a plurality of solutions including bicarbonate, carbonate, and varying amounts of sodium chloride (NaCl) with respect to pH, according to one or more implementations disclosed.

FIG. 2 illustrates a plot of the chemical shift of each of the plurality of solutions including a carboxyl group with respect to pH.

It should be appreciated, based on equations (1)-(5), that the pH is determined by a molar ration of the chemical species of samples and/or solutions whose chemical shift is sensitive to pH. Unlike the conventional method of measuring the pH via an electrode, the methods disclosed herein are not dependent upon the amount of hydrogen ions. As such, it should be appreciated that the methods disclosed herein may be used to accurately determine pH in samples and/or solutions having a low water content (e.g., less than 80 weight %).

Preparing the calibration curve may further include fitting a curve to the plot of the chemical shift of each of the plurality of solutions with respect to the pH of each of the plurality of solutions. Fitting the curve may include applying a nonlinear least square analysis to the plot. Fitting the curve to the plot may allow the determination of one or more variables or values of Equation (2), (4), and/or (5). For example, the nonlinear least square fit may be applied to determine the values of the pKa, the $\delta CO_3^{2-}$, and the $\delta HCO_3^-$ in Equation (2). Further, the nonlinear least square fit may be applied to determine the values of the pKa, the $\delta H_2PO_4^-$, and the $\delta HPO_4^{2-}$ of Equation (4). The nonlinear least square fit may further be applied to determine the values of the pKa, the $\delta CO_2H$, and the $\delta CO_2^-$ of Equation (5)

Determining Chemical Shift

The method may include determining a chemical shift of the composition, including but not limited to a gel, a paste, a colloid, and/or an aqueous solution, including the chemical species or molecular entity. The chemical shift of the composition may be determined by nuclear magnetic resonance (NMR). For example, compositions including bicarbonate or carbonate as the chemical species or molecular entity may utilize carbon-13 NMR spectroscopy. In another example, compositions including a chemical species or molecular entity having a phosphate group may utilize phosphorus-31 NMR spectroscopy. It should be appreciated, that the type of NMR utilized may be determined, at least in part, by the one or more chemical species or molecular entities contained in the gel, paste, colloid, and aqueous solution and/or the one or more chemical species or molecular entities utilized to prepare the calibration curve. It should further be appreciated that while carbon-13 NMR spectroscopy and phosphorus-31 NMR spectroscopy are demonstrated below, it should be appreciated that other types of NMR may be utilized, such as NMR that measures the chemical shift of any one or more of hydrogen nuclei, fluorine, boron, nitrogen, oxygen, tin, or the like, each of which have distinctive magnetic properties.

In at least one implementation, when analyzing a composition, including but not limited to a gel, a paste, a colloid, and/or an aqueous solution, the chemical shift of the composition may be performed without any pre-processing of the composition. For example, the chemical shift of the composition may be measured without diluting, filtering, buffering, or otherwise modifying the composition. In another example, the chemical shift of the composition may be measured as is or as a neat composition, for example a neat oral care product. For example, the oral care product may be a toothpaste or tooth gel, and the chemical shift may be measured by directly measuring the toothpaste or the tooth gel in the NMR spectrometer.

In another implementation, the composition may be pre-processed prior to measuring the chemical shift. For example, if the composition is an oral care product, the oral care product may be diluted or combined with water to prepare a slurry, and the chemical shift of the slurry may be measured. In another example, the composition may be aged for at least 1 day, at least 2 days, at least 3 days, at least 4 days, at least 5 days, at least 10 days, at least 30 days, at least 60 days, or more prior to measuring the chemical shift thereof. The composition may be aged at any temperature. For example, the composition may be aged at room temperature (RT). In another example, the composition may be aged at a temperature below 0° C., at about 0° C., greater than 0° C., greater than 10° C., greater than 30° C., greater than 50° C., or more.

The measured chemical shift of the composition may then be utilized to determine the pH of the composition. For example, the measured chemical shift of the composition may be utilized to directly determine the pH of the composition with the calibration curve.

All ingredients for use in the compositions and methods described herein should be orally acceptable. As used herein, "orally acceptable" may refer any ingredient that is present in a composition as described in an amount and form, which does not render the composition unsafe for use in the oral cavity.

EXAMPLES

The examples and other implementations described herein are exemplary and not intended to be limiting in describing the full scope of compositions and methods of this disclosure. Equivalent changes, modifications and variations of specific implementations, materials, compositions and methods may be made within the scope of the present disclosure, with substantially similar results.

Example 1

A calibration curve was prepared for measuring bicarbonate with an NMR by using standardized samples of $NaHCO_3$ in water maintained at varying pH. The solutions included about 0.5 weight % sodium bicarbonate, and the pH was varied using hydrochloric acid (HCl) and sodium hydroxide (NaOH). NMR was performed on the samples to obtain C-13 chemical shift values. A pH electrode was utilized to measure the pH of each of the standardized samples, and the calibration curve was prepared by correlating the measured C-13 chemical shift to the pH values measured by the pH electrode, as illustrated in FIG. 1. As such, the observed $^{13}C$ chemical shift of the carbonyl group ($\delta_C$) was expressed as the weighted average of the $^{13}C$ chemical shift between $HCO_3^-$ ($\delta HCO_3^-$) and $CO_3^{2-}$ ($\delta CO_3^2$). The pH of the bicarbonate was described in terms of pKa of bicarbonate, as represented by Equation 2.

$$pH = pKa + \log[(\delta_C - \delta HCO_3^-)/(\delta CO_3^{2-} - \delta_C)] \quad (2).$$

The nonlinear least squares fit was applied to determine the values of the pKa, the $\delta CO_3^{2-}$, and the $\delta HCO_3^-$. The values of each are summarized in Table 1. The $^{13}C$ chemical shift of bicarbonate as a function of pH with a fitted curve is illustrated in FIG. 1. The plot of FIG. 1 and the corresponding $R^2$ indicated that sodium bicarbonate represented a reliable candidate for measuring pH via $^{13}C$ NMR.

TABLE 1

Variables for Parameters in Equation 1

| Parameter | Value |
|---|---|
| pKa | 10.36 |
| $\delta\,CO_3^{2-}$ | 160.25 |
| $\delta\,HCO_3^-$ | 168.24 |
| $R^2$ | 0.98 |

To assess any interferences or interactions between the sodium bicarbonate with other major components of the toothpaste compositions (1)-(10), the $^{13}C$ NMR chemical shift of $NaHCO_3$ was measured in the presence of varying amounts of sodium chloride (NaCl). Particularly, the $^{13}C$ NMR chemical shift of $NaHCO_3$ including sodium chloride in amounts up to about 20 weight % was evaluated and illustrated in FIG. 2. As surprisingly and unexpectedly illustrated in FIG. 2, the presence of sodium chloride in amounts of about 5 weight %, about 10 weight %, and about 20 weight % did not indicate any notable changes or deviations in the $^{13}C$ NMR chemical shift of bicarbonate. This further reinforced that bicarbonate is a reliable candidate for measuring pH via $^{13}C$ NMR.

In addition to the foregoing, the $^{13}C$ NMR chemical shift of $NaHCO_3$ was measured in the presence of 1.5% and 8% Arginine at varying pH. The $^{13}C$ NMR chemical shift of bicarbonate including varying amounts of Arginine as a function of pH is illustrated in FIG. 3. As surprisingly and unexpectedly illustrated in FIG. 3, the presence of Arginine at 1.5% and at 8% did not indicate any notable changes or deviations in the $^{13}C$ chemical shift of bicarbonate. This further reinforced that bicarbonate is a reliable candidate for measuring pH via $^{13}C$ NMR.

Example 2

Ten oral care compositions (1)-(10) were prepared or obtained for evaluating the pH. Particularly, ten toothpaste compositions (1)-(10) were prepared or obtained for testing. Each of the toothpaste compositions (1)-(10) included sodium bicarbonate in an amount of greater than 0.5 weight %, and water in an amount of from about 14 weight % to about 18 weight %. The key ingredients contained in each of the toothpaste compositions (1)-(10) are summarized in Table 1.

TABLE 1

Key Ingredients in Toothpaste Compositions (1)-(10)

| Toothpaste Composition | Arginine (wt %) | Sodium Bicarbonate $NaHCO_3$ (wt %) | Arginine Bicarbonate (wt %) | Phosphoric acid ($H_3PO_4$) (wt %) |
|---|---|---|---|---|
| (1) | 0 | 0.5 | 19.5 | 0 |
| (2) | 0 | 0.5 | 0 | 0 |
| (3) | 0 | 0.5 | 19.5 | 0 |
| (4) | 0 | 0.5 | 1.5 | 0 |
| (5) | 0 | 1.0 | 0 | 0.3 |
| (6) | 1.5 | 0.5 | 0 | 0.3 |
| (7) | 1.5 | 0.75 | 0 | 0.3 |
| (8) | 1.5 | 1.0 | 0 | 0.3 |
| (9) | 1.5 | 0.5 | 0 | 0.3 |
| (10) | 1.5 | 0.5 | 0 | 0 |

Example 3

The pH of each of the toothpaste compositions (1)-(10) as a neat paste (without dilution) and as a slurry was measured via a conventional pH meter. The pH meter or electrode utilized was a benchtop pH meter (Mettler Toledo, F20, Switzerland) with a glass pH electrode (ORION, Thermo Fisher). It should be appreciated that prior to measuring the pH, the pH meter was calibrated using standard buffer solutions, and each of the measurements were performed in triplicate at room temperature to obtain a mean pH value. It should further be appreciated that between each of the measurements, the tip of the pH electrode was thoroughly washed with distilled water and acetone, and subsequently dried.

To determine the pH of each of the toothpaste compositions (1)-(10) as a neat paste (without dilution), the pH electrode of the pH meter inserted directly into the respective tube of each of the toothpaste compositions (1)-(10) such that the pH electrode was in full contact with the paste for at least 5 minutes to allow the measured pH value to stabilize. To prepare a slurry of each of the toothpaste compositions (1)-(10), 9 grams (g) of distilled water and 1 g of the respective toothpaste composition (1)-(10) was combined with one another in a glass vial and stirred at 25° C. for about 10 minutes. To determine the pH of each of the toothpaste compositions (1)-(10) as a slurry, the pH electrode was placed in the slurry under stirring. The results of the pH measured via the pH meter are summarized in Table 2.

Example 4

The pH of each of the toothpaste compositions (1)-(10) as a neat paste (without dilution) and as a slurry was measured via $^{13}C$ NMR. NMR measurements were performed on an AVANCE NEO® NMR Spectrometer obtained from Bruker Biospin Corp. of Billerica, MA, USA. The NMR Spectrometer was operated with a 5 mm CryoProbe operating at 500.13 MHz for $^1H$ and 125.8 MHz for $^{13}C$ at 25° C. The $^{13}C$ NMR spectra of each of the toothpaste compositions (1)-(10) was acquired using zgig pulse sequence with a proton decoupling during the acquisition to avoid signal build-up due to NOE effect. The following parameters of the NMR Spectrometer were maintained during the measurements: Pulse Length=5 μs; Recycle Delay=20 sec; Number of Scans=64. It should be appreciated that each of the $^{13}C$ NMR spectrum was acquired for about 15 to about 20 min to ensure that a sufficient signal-to-noise ratio was obtained for recording $^{13}C$ NMR chemical shift values of the bicarbonate ($HCO_3^{2-}$). $^{13}C$ chemical shift was referenced to 1% Tetramethylsilane as zero.

To determine the pH of each of the toothpaste compositions (1)-(10) as a neat paste (without dilution), 1 g of each of the toothpaste compositions (1)-(10) was disposed into respective 5 mm NMR tubes with a syringe, and gently centrifuged (about 1,000 rpm) for about 1 minute (min) to ensure that the paste was settled at the bottom of the NMR tube without any phase separation. To prepare a slurry of each of the toothpaste compositions (1)-(10), each of the toothpaste compositions (1)-(10) was combined with at a 1:9 weight ratio (toothpaste:water) without centrifugation. The results of the pH measured via the pH meter are summarized in Table 2.

TABLE 2 pH of Toothpaste Compositions (1)-(10) Measured via pH Meter and $^{13}C$ NMR

| | NMR Method | | | | pH Meter Method | | | |
|---|---|---|---|---|---|---|---|---|
| | TP (Neat) | | TP (Slurry) | | TP (Neat) | | TP (Slurry) | |
| # | pH | SD | pH | SD | pH | SD | pH | SD |
| (1) | 9.62 | 0.006 | 9.34 | 0.006 | 9.05 | 0.08 | 8.74 | 0.07 |
| (2) | 9.50 | 0.005 | 9.50 | 0.008 | 9.23 | 0.19 | 8.81 | 0.11 |
| (3) | 9.58 | 0.004 | — | 0.009 | 9.19 | 0.12 | 8.69 | 0.11 |
| (4) | 10.02 | 0.006 | 9.64 | 0.008 | 9.37 | 0.09 | 8.91 | 0.06 |
| (5) | 9.97 | 0.003 | 9.94 | 0.009 | 9.73 | 0.07 | 9.04 | 0.05 |
| (6) | 10.19 | 0.013 | 9.87 | 0.017 | 9.66 | 0.13 | 9.43 | 0.13 |
| (7) | 10.18 | 0.006 | 9.84 | 0.009 | 9.59 | 0.11 | 9.27 | 0.06 |
| (8) | 10.19 | 0.004 | 9.85 | 0.006 | 9.64 | 0.08 | 9.19 | 0.08 |
| (9) | 10.04 | 0.003 | — | 0.005 | 9.34 | 0.07 | 9.08 | 0.06 |
| (10) | 10.21 | 0.001 | — | 0.008 | 9.61 | 0.13 | 9.36 | 0.14 |

As illustrated in Table 2, the standard deviations (SD) of the pH measured via the NMR method were unexpectedly, significantly, and surprisingly lower than the SD of the pH measured via the pH meter method. In some cases the SD of the pH measured via the NMR method was at least one magnitude less than the SD of the pH measured via the pH meter method. It should be appreciated that the SD indicates the precision, accuracy, reliability and/or reproducibility of measuring the pH via the NMR method relative to the pH meter method.

Example 5

A calibration curve was prepared for measuring phosphate groups with an NMR by using standardized buffered solutions of sodium phosphate monobasic ($NaH_2PO_4$) and disodium hydrogen phosphate ($Na_2HPO_4$) at varying pH. A P-31 NMR pH titration experiment was conducted on the phosphate buffer having a concentration of 100 mM phosphate at various pH (i.e., pH of about 5 to about 8.5) adjusted using $NaH_2PO_4$ and $Na_2HPO_4$ in water. $NaH_2PO_4$ and $Na_2HPO_4$ undergo a relatively fast exchange in the NMR timescale. As such, the observed $^{31}P$ chemical shift of the phosphate group (op) was expressed as the weighted average of $^{31}P$ chemical shift between $H_2PO_4^-$ ($\delta H_2PO_4^-$) and $HPO_4^{2-}$ ($\delta HPO_4^{2-}$). The pH of the phosphate group was described in terms of pKa of phosphate, as represented by Equation 4.

$$pH = pKa + \log[(\delta_P - \delta H_2PO_4^-)/(\delta HPO_4^{2-} - \delta_P)] \quad (4)$$

The nonlinear Least Squares Fit was applied to determine the values of the pKa, the $\delta H_2PO_4^-$, and the $\delta HPO_4^{2-}$. The values of each are summarized in Table 3. The $^{31}P$ chemical shift of phosphate as a function of pH with a fitted curve is illustrated in FIG. 3. The plot of FIG. 3 and the corresponding $R^2$ indicated that phosphate represented a reliable candidate for measuring pH via $^{31}P$ NMR.

TABLE 3

Variables for Parameters in Equation 2

| Parameter | Value |
|---|---|
| pKa | 6.82 |
| $\delta H_2PO_4^-$ | −0.0479 |
| $\delta HPO_4^{2-}$ | 2.437 |
| $R^2$ | 0.99 |

Example 6

Eight oral care compositions (11)-(18) were prepared or obtained for evaluating the pH. Particularly, eight toothpaste compositions (11)-(18) were prepared or obtained for testing. Each of the toothpaste compositions (11)-(18) included water in an amount of from about 14 weight % to about 20 weight %. The key ingredients contained in the toothpaste compositions (11)-(18) include arginine (Arg), tetrasodium pyrophosphate (TSPP), phosphoric acid ($H_3PO_4$), sodium monofluorophosphate (MFP), and dicalcium phosphate dehydrate (Dical) the contents of the ingredients contained in each of the toothpaste compositions (11)-(18) is summarized in Table 3.

TABLE 3

Key Ingredients in Toothpaste Compositions (11)-(18)

| Toothpaste Composition | Arg (wt %) | TSPP (wt %) | 85% $H_3PO_4$ (wt %) | MFP (wt %) | Dical (wt %) |
|---|---|---|---|---|---|
| (11) | 1.5 | 0.25 | 0.6 | 0.76 | 40 |
| (12) Aged | 1.5 | 0.25 | 0.6 | 0.76 | 40 |
| (13) | 1.5 | 0.25 | 0.7 | 0.76 | 40 |
| (14) Aged | 1.5 | 0.25 | 0.7 | 0.76 | 40 |
| (15) Aged RT for 9 mo. | 1.5 | 0 | 0.3 | 0.76 | 40 |
| (16) | — | 0.25 | — | 0.76 | 40 |
| (17) Aged | — | 0.25 | — | 0.76 | 40 |
| (18) | — | 0.25 | — | — | — |

It should be appreciated that toothpaste compositions (12), (14), and (17) include the same composition as (11), (13), and (16), respectively, but toothpaste compositions (12), (14), and (17) were aged. Specifically, toothpaste compositions (12) and (14) were aged at about 49° C. for 6 weeks, and toothpaste composition (17) was aged at room temperature (RT) for one year.

As indicated in Table 3, toothpaste compositions (11)-(15) included phosphoric acid and tetrasodium pyrophosphate (TSPP), toothpaste compositions (16)-(18) included at least TSPP and Dical, and toothpaste compositions (16) (17) included TSPP, Dical, and MFP. It should be appreciated that toothpaste composition (18) only included TSPP, which partially degrades to orthophosphate as a by-product. Further, MFP also partially degrades to orthophosphate as a by-product.

Example 7

The pH of each of the toothpaste compositions (11)-(18) as a neat paste (without dilution) and as a slurry was measured via a conventional pH meter. It should be appreciated that prior to measuring the pH, the pH meter was calibrated using standard buffer solutions, and each of the measurements was performed in triplicate to obtain a mean pH value. It should further be appreciated that between each of the measurements, the tip of the pH electrode was thoroughly washed with distilled water and acetone, and subsequently dried.

To determine the pH of each of the toothpaste compositions (11)-(18) as a neat paste (without dilution), the pH electrode of the pH meter was inserted directly into the respective tube of each of the toothpaste compositions (11)-(18) such that the pH electrode was in full contact with the paste for at least 5 minutes to allow the measured pH value to stabilize. To prepare a slurry of each of the toothpaste compositions (11)-(18), 9 grams (g) of distilled water and 1 g of the respective toothpaste composition (11)-(18) was combined with one another in a glass vial and stirred at 25° C. for about 10 minutes. To determine the pH of each of the toothpaste compositions (11)-(18) as a slurry, the pH electrode was placed in the slurry under stirring. The results of the pH measured via the pH meter are summarized in Table 4.

Example 8

The pH of each of the toothpaste compositions (11)-(18) as a neat paste (without dilution) and as a slurry was measured via $^{31}P$ NMR. NMR measurements were performed on an AVANCE NEO® NMR Spectrometer obtained from Bruker Biospin Corp. of Billerica, MA, USA. The NMR Spectrometer was operated with a 5 mm CryoProbe operating at 500.13 MHz for $^1H$ and 202.46 MHz for $^{31}P$ at 25° C. The $^{31}P$ NMR spectra of each of the toothpaste compositions (11)-(18) was acquired using zg pulse sequence. The following parameters of the NMR Spectrometer were maintained during the measurements: Pulse Length=5 µs; Recycle Delay=30 sec; Number of Scans=8. It should be appreciated that each of the $^{31}P$ NMR spectrum was acquired for about 2 min to ensure that a sufficient signal-to-noise ratio was obtained for recording $^{31}P$ NMR chemical shift values of the phosphate. $^{31}P$ chemical shift was referenced to 85% $H_3PO_4$ as zero.

To determine the pH of each of the toothpaste compositions (11)-(18) as a neat paste (without dilution), 1 g of each of the toothpaste compositions (11)-(18) was disposed into respective 5 mm NMR tubes with a syringe, and gently centrifuged (about 1,000 rpm) for about 1 minute (min) to ensure that the paste was settled at the bottom of the NMR tube without any phase separation. To prepare a slurry of each of the toothpaste compositions (11)-(18), each of the toothpaste compositions (11)-(18) was combined with water at a 1:9 weight ratio (toothpaste:water) without centrifugation. The results of the pH measured via the pH meter are summarized in Table 4.

TABLE 4 pH of Toothpaste Compositions (11)-(18) Measured via pH Meter and $^{13}C$ NMR

| Toothpaste Composition | NMR Method | | | | pH Meter Method | | | |
|---|---|---|---|---|---|---|---|---|
| | TP (Neat) | | TP (Slurry) | | TP (Neat) | | TP (Slurry) | |
| | pH | SD | pH | SD | pH | SD | pH | SD |
| (11) | 7.05 | 0.005 | 7.16 | 0.011 | 6.65 | 0.05 | 7.19 | 0.08 |
| (12) Aged | 6.67 | 0.004 | 6.79 | 0.003 | 6.62 | 0.2 | 6.95 | 0.11 |
| (13) | 6.88 | 0.011 | 7.03 | 0.009 | 6.43 | 0.08 | 4.08 | 0.07 |
| (14) Aged | 6.58 | 0.003 | 6.75 | 0.003 | 6.19 | 0.07 | 6.83 | 0.13 |
| (15) Aged RT for 9 mo. | 6.74 | 0.016 | 6.99 | 0.008 | 6.42 | 0.08 | 7.09 | 0.09 |
| (16) | 7.56 | 0.005 | 7.56 | 0.008 | 7.51 | 0.11 | 7.7 | 0.09 |
| (17) Aged | 6.04 | 0.002 | 6.31 | 0.005 | 5.89 | 0.06 | 6.42 | 0.08 |
| (18) | 6.88 | 0.004 | 6.72 | 0.004 | 6.53 | 0.05 | 6.96 | 0.07 |

It should be appreciated that the estimated pH of toothpaste composition (11) and (13) is about 7.0 and 6.5, respectively. As illustrated in Table 4, while the NMR method and the pH meter method both exhibited the same pH trend of showing that the toothpaste composition (13) is relatively more acidic than toothpaste composition (11), the pH measured through the NMR method were closer or more accurate with respect to the estimated pH. Further, the standard deviations (SD) of the pH measured via the NMR method were unexpectedly, significantly, and surprisingly lower than the SD of the pH measured via the pH meter method.

As further illustrated in Table 4, after aging, the pH of each of the toothpaste compositions (12) and (14) decreased to about 6.5. Without being bound by theory, it is believed that the flavor compound (i.e., wintergreen oil) partially decomposed to produce salicylate acid upon aging, which resulted in the reduced pH.

As discussed above, some of the toothpaste compositions (16)-(18) did not include phosphoric acid. As such, it was surprisingly and unexpectedly discovered that the method of measuring the pH of the toothpaste compositions (16)-(18) could be extended to other phosphate species, namely, orthophosphate ($PO_4$), which is formed as a by-product in toothpastes containing MFP, Dical, and TSPP.

Example 9

Figure 4:
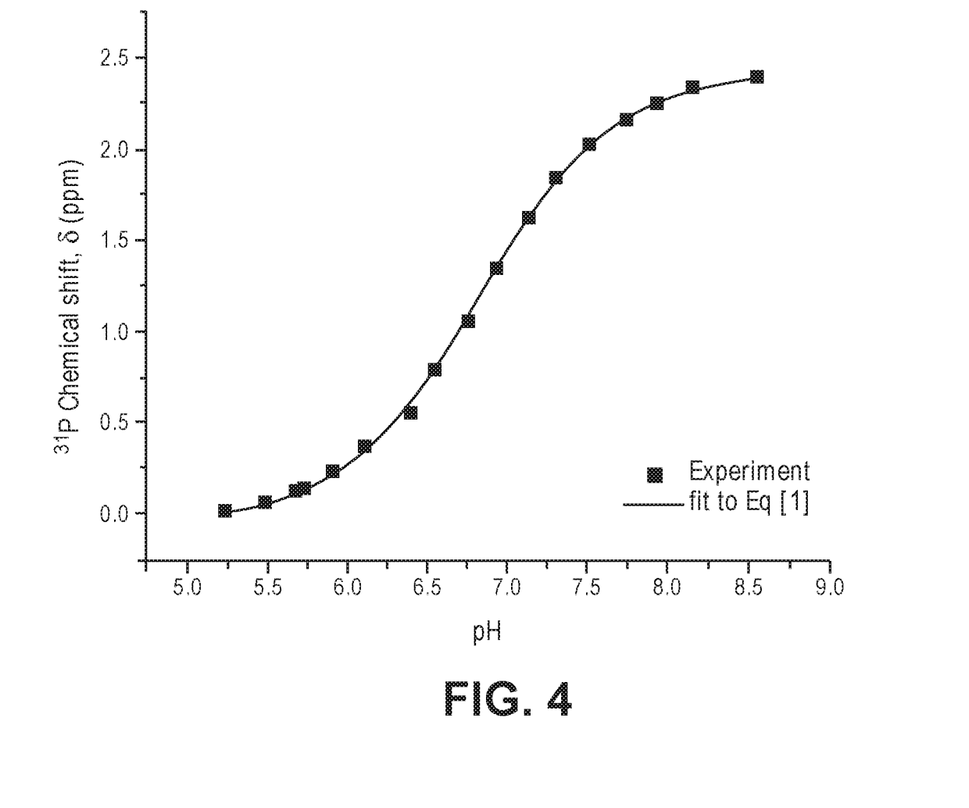
FIG. 4 illustrates a plot of the chemical shift of each of the plurality of solutions including a phosphate group with respect to pH, according to one or more implementations disclosed.
Figure 5:
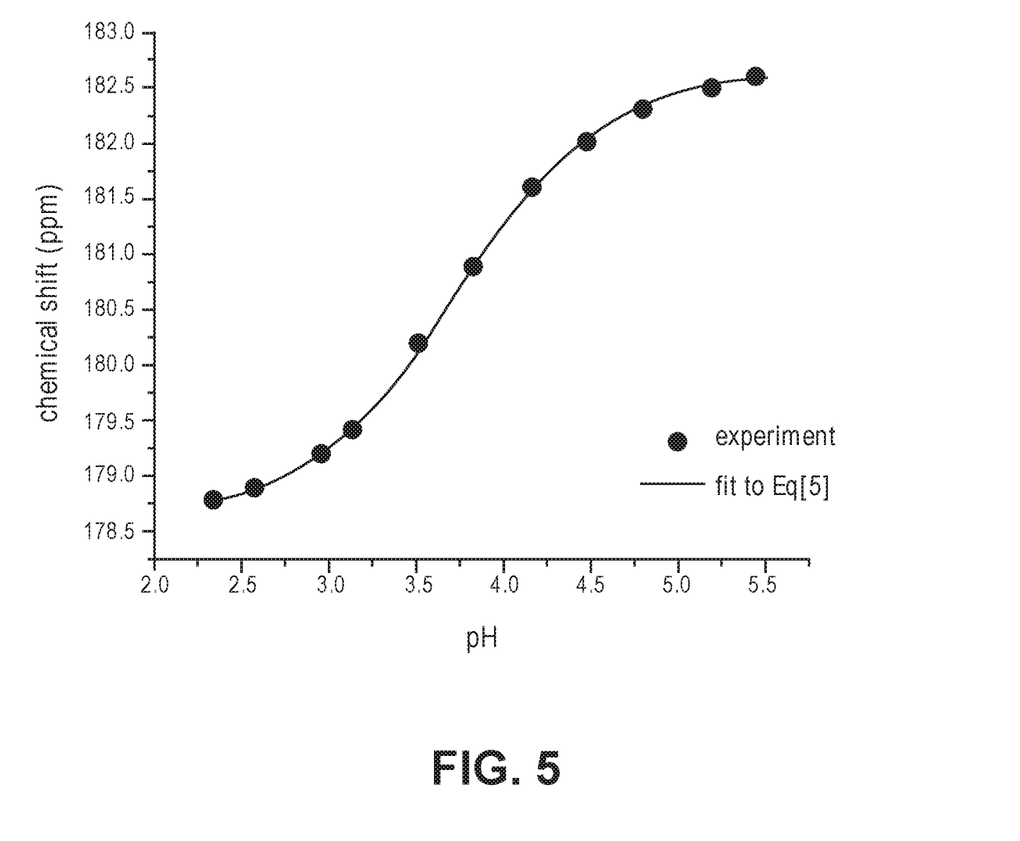
FIG. 5 illustrates a plot of the chemical shift of each of the plurality of solutions including lactic acid with respect to pH, according to one or more implementations disclosed.

A calibration curve was prepared for measuring lactic acid with an NMR by using standardized buffered solutions of sodium lactate and lactic acid at different mole ratios in water at varying pH. The solutions included a total concentration of sodium lactate and lactic acid at about 1 weight %, and the pH was varied from a pH of about 2 to about 5.5. NMR was performed on the samples to obtain C-13 chemical shift values. A pH electrode was utilized to measure the pH of each of the standardized samples, and the calibration curve was prepared by correlating the measured C-13 chemical shift to the pH values measured by the pH electrode, as illustrated in FIG. 4. As such, the observed $^{13}C$ chemical shift of the carbonyl group ($\delta_C$) was expressed as the weighted average of the $^{13}C$ chemical shift between $CO_2H$ ($\delta CO_2H$) and $CO_2^-$ ($\delta CO_2^-$). The pH of the carboxyl group was described in terms of pKa of the carboxyl group, as represented by Equation 5.

$$pH = pKa + \log\left[(\delta_C - \delta CO_2H)/(\delta CO_2^- - \delta_C)\right] \quad (5)$$

The nonlinear least squares fit was applied to determine the values of the pKa, the $\delta CO_2^-$, and the $\delta CO_2H$. The values of each are summarized in Table 5. The $^{13}C$ chemical shift of the carboxyl group as a function of pH with a fitted curve is illustrated in FIG. 4. The plot of FIG. 4 and the corresponding $R^2$ indicated that the carboxyl group of lactic acid represented a reliable candidate for measuring pH via $^{13}C$ NMR.

TABLE 5

Variables for Parameters in Equation 1

| Parameter | Value |
|---|---|
| pKa | 3.73 |
| δ $CO_2^-$ | 178.62 |
| δ $CO_2H$ | 182.67 |
| $R^2$ | 0.99 |

Example 10

Four personal care compositions (19)-(22) were prepared or obtained for evaluating the pH. Each of the personal care compositions (19)-(22) included lactic acid in an amount of greater than 0.8 weight % and water in an amount of from about 68.5 weight % to about 74.5 weight %. The key ingredients contained in each of the personal care compositions (19)-(22) are summarized in Table 6.

TABLE 6

Key Ingredients in Personal Care Compositions (19)-(22)

| Personal Care Composition | Lactic Acid (wt %) | Sodium Laureth Sulfate (wt %) | Cocamidopropyl betaine (wt %) | Water (wt %) |
|---|---|---|---|---|
| (19) | 0.8 | 7.9 | 2.9 | 68.5 |
| (20) | 0.8 | 7.9 | 2.9 | 68.5 |
| (21) | 1.0 | 11.3 | 9.7 | 74.5 |
| (22) | 1.0 | 11.3 | 9.7 | 74.5 |

The pH of each of the personal care compositions (19)-(22) as a neat gel (without dilution) was measured via a pH meter according to the procedures described above. The pH of each of the personal care compositions (19)-(22) as a neat gel was also measured via $^{13}C$ NMR. NMR measurements were performed according to the procedures described above. The results of the pH measured via the pH meter are summarized in Table 2.

TABLE 7 pH of Personal Care Compositions (19)-(22) Measured via pH Meter and $^{13}C$ NMR

| | pH Meter Method | | NMR Method | |
|---|---|---|---|---|
| # | pH | SD | pH | SD |
| (19) | 5.10 | 0.07 | 5.30 | 0.005 |
| (20) | 4.30 | 0.06 | 4.22 | 0.005 |
| (21) | 3.60 | 0.10 | 3.77 | 0.004 |
| (22) | 3.80 | 0.05 | 3.74 | 0.006 |

The present disclosure has been described with reference to exemplary implementations. Although a limited number of implementations have been shown and described, it will be appreciated by those skilled in the art that changes may be made in these implementations without departing from the principles and spirit of the preceding detailed description. It is intended that the present disclosure be construed as including all such modifications and alterations insofar as they come within the scope of the appended claims or the equivalents thereof.

What is claimed is:

1. A method for determining pH of a composition, the method comprising:
preparing a calibration curve of a chemical species comprising an acid dissociation constant, wherein preparing the calibration curve comprises plotting a chemical shift of the chemical species relative to pH;
determining a chemical shift of a composition comprising the chemical species; and
determining the pH of the composition with the chemical shift of the composition and the calibration curve;
wherein the composition is a gel, paste, colloid, or aqueous solution and is selected from the group consisting of an oral care product, a home care product, a personal care product, and combinations thereof.

2. The method of claim 1, wherein the chemical species comprises a carbonyl group, optionally, a carboxyl group.

3. The method of claim 1, wherein the chemical species comprises a bicarbonate ion or a carbonate ion.

4. The method of claim 1, wherein the chemical shift of the composition is determined with carbon-13 nuclear magnetic resonance spectroscopy ($^{13}C$ NMR).

5. The method of claim 1, wherein the chemical species comprises a phosphate group.

6. The method of claim 1, wherein the chemical species comprises one or more of tetrasodium pyrophosphate, tetrapotassium pyrophosphate, phosphoric acid, sodium monofluorophosphate, dicalcium phosphate dehydrate, sodium triphosphate, sodium hexametaphosphate, or combinations thereof.

7. The method of claim 6, wherein the chemical species comprises phosphoric acid.

8. The method of claim 1, wherein the chemical shift of the composition is determined with phosphorus-31 nuclear magnetic resonance spectroscopy ($^{31}P$ NMR).

9. The method of claim 1, wherein the composition comprises water in an amount less than 80 weight %, optionally, less than 70 weight %, less than 60 weight %, or less than 50 weight %, based on a total weight of the composition.

10. The method of claim 1, wherein the chemical shift of the oral care product, home care product, personal care product, or combination thereof is determined without diluting the oral care product, home care product, personal care product, or combination thereof.

11. The method of claim 1, wherein the chemical shift of the oral care product, home care product, personal care product, or combination thereof is determined without preprocessing the oral care product, home care product, personal care product, or combination thereof.

12. The method of claim 1, wherein determining the chemical shift of the oral care product, home care product, personal care product, or combination thereof comprising the chemical species comprises preparing a slurry of the oral care product, home care product, personal care product, or combination thereof.

13. The method of claim 1, wherein preparing the calibration curve of the chemical species further comprises:
preparing a plurality of solutions comprising the chemical species, wherein each of the plurality of solutions comprises a different pH; and
determining a chemical shift of each of the plurality of solutions comprising the different pH.

14. The method of claim 13, wherein preparing the calibration curve of the chemical species further comprises:

preparing a plot of the chemical shift of each of the plurality of solutions with respect to the pH of each of the plurality of solutions; and fitting a curve to the plot to prepare the calibration curve.

* * * * *